(12) United States Patent
Zhang et al.

(10) Patent No.: US 10,906,043 B2
(45) Date of Patent: Feb. 2, 2021

(54) MICROFLUIDIC BASED INTEGRATED SAMPLE ANALYSIS SYSTEM

(71) Applicants: Gong Zhang, Winnipeg (CA); Francis Lin, Winnipeg (CA); Edward Stewart Richmond, Winnipeg (CA); Marshall Ring, Winnipeg (CA)

(72) Inventors: Gong Zhang, Winnipeg (CA); Francis Lin, Winnipeg (CA); Edward Stewart Richmond, Winnipeg (CA); Marshall Ring, Winnipeg (CA)

(73) Assignee: Biomed Canada Corporation, Winnipeg (CA)

( * ) Notice: Subject to any disclaimer, the term of this patent is extended or adjusted under 35 U.S.C. 154(b) by 540 days.

(21) Appl. No.: 14/759,815

(22) PCT Filed: Jan. 13, 2014

(86) PCT No.: PCT/CA2014/050018
§ 371 (c)(1),
(2) Date: Jul. 8, 2015

(87) PCT Pub. No.: WO2014/107812
PCT Pub. Date: Jul. 17, 2014

(65) Prior Publication Data
US 2017/0001196 A1  Jan. 5, 2017

Related U.S. Application Data

(60) Provisional application No. 61/751,445, filed on Jan. 11, 2013.

(51) Int. Cl.
*B01L 3/00* (2006.01)
*G01N 33/543* (2006.01)
(Continued)

(52) U.S. Cl.
CPC ... *B01L 3/502761* (2013.01); *B01L 3/502715* (2013.01); *B01L 3/502738* (2013.01);
(Continued)

(58) Field of Classification Search
CPC ......... G01N 21/645; G01N 2021/6482; G01N 2201/0627; B01L 3/502746;
(Continued)

(56) References Cited

U.S. PATENT DOCUMENTS

2002/0049389 A1* 4/2002 Abreu ................. A61B 3/1241
                                                        600/558
2004/0092033 A1* 5/2004 Gustafson .......... B01D 19/0031
                                                        436/180
(Continued)

OTHER PUBLICATIONS

El-Ali, J. . Cells on chips. Nature. Jul. 27, 2006(Jul. 27, 2006). vol. 442(7101), 403-411.*

*Primary Examiner* — Rebecca M Fritchman
(74) *Attorney, Agent, or Firm* — Michael R Williams; Kyle R Satterthwaite; Ade & Company Inc.

(57) ABSTRACT

A portable microfluidic system capable of rapid diagnosis is described, which is able to analyze genetic, protein and cell composition of a sample in parallel for specific diseases from a relatively small sample. The method uses a single microfluidic chip integrated into a unique portable microfluidic platform and provides improved diagnostic accuracy, allows for frequent monitoring and is suitable for easy use in clinical settings.

3 Claims, 3 Drawing Sheets

(51) Int. Cl.
*G01N 21/64* (2006.01)
*B01L 7/00* (2006.01)
*C12Q 1/686* (2018.01)

(52) U.S. Cl.
CPC ... *B01L 3/502746* (2013.01); *B01L 3/502753* (2013.01); *B01L 7/52* (2013.01); *C12Q 1/686* (2013.01); *G01N 21/645* (2013.01); *G01N 21/6428* (2013.01); *G01N 33/54366* (2013.01); *B01L 2200/10* (2013.01); *B01L 2300/0654* (2013.01); *B01L 2300/0816* (2013.01); *B01L 2300/0861* (2013.01); *B01L 2300/0864* (2013.01); *B01L 2300/0887* (2013.01); *B01L 2300/18* (2013.01); *B01L 2400/0406* (2013.01); *B01L 2400/0457* (2013.01); *B01L 2400/084* (2013.01); *B01L 2400/086* (2013.01); *G01N 2021/6439* (2013.01); *G01N 2021/6482* (2013.01); *G01N 2201/0627* (2013.01)

(58) Field of Classification Search
CPC ............... B01L 3/502753; B01L 7/52; B01L 2300/0816; B01L 2300/0864
See application file for complete search history.

(56) References Cited

U.S. PATENT DOCUMENTS

| | | | |
|---|---|---|---|
| 2006/0210984 A1* | 9/2006 | Lambert | B01L 3/5027 435/6.12 |
| 2009/0130745 A1* | 5/2009 | Williams | B01L 3/5027 435/287.2 |

* cited by examiner

Fig. 1.

Design of integrated microfluidic chip

Fig. 2

1) A and B both open, flow via L1
2) A close, B open, flow via L2

MICROFLUIDIC BASED INTEGRATED SAMPLE ANALYSIS SYSTEM

The instant application is a 371 of PCT Application PCT/CA2014/050018, filed Jan. 13, 2014, now abandoned, which claimed the benefit of U.S. Provisional Patent Application 61/751,445, filed Jan. 11, 2013, now abandoned.

BACKGROUND OF THE INVENTION

PCR machines are typically used for DNA sequence analysis and for testing for the presence of viruses. Generally, PCR machines are expensive and require sterile labs for testing since the process uses open vials and contamination risks are high. These tests also require skilled technicians.

Tests to detect specific proteins of interest typically require antibody-based immune assays which makes this type of data costly to acquire.

Tests to analyze cell behavior or detect specific cell types of interest require a microscope and a lab technician, meaning that this type of data is also very costly to acquire.

Thus, existing conventional diagnosis methods are often time-consuming, expensive, require specialized facilities and large amounts of sample(s), and often result in inconsistent results (as many steps of the assays depend on the skill of the operators). Microfluidics-based methods have the advantages of miniaturization, cost efficiency, faster results analysis and test condition controls (i.e. the reaction environment is precisely controlled and the assays can be conveniently automated for high-throughput). Microfluidics therefore offers the ability to take the lab to the sample compared to taking the sample to the lab.

Microfluidic systems able to detect disease-relevant genes or proteins or cells have been developed. However, the current art is limited to single marker-based detection of genes, proteins and cells. This current art has limitations in that MFC cannot complete multiple analysis of different biomarkers from the same sample. This is important since diagnosis of a disease often requires the concurrent identification of multiple biomarkers. The current art requires one sample to detect one specific biomarker, as no MFCs can identify multiple biomarkers concurrently from the same sample.

More precisely, current methods rely on separate diagnostic chips specific to a gene, protein or cell(s), sometimes resulting in inaccuracies from the use of different samples and the complex inter-relatedness of the biomarkers (i.e. gene expression does not necessarily lead to functional protein expression and/or cell functions and vice versa). Currently, there are no microfluidic systems available that can analyze genes, proteins and cells from the same sample on a single chip for diagnosis.

Consequently, in the prior art methods, multiple samples must be taken from a patient for analysis. This can be time consuming and uncomfortable for the patient. In addition, multiple samples for multiple separate analyses has an inherent risk of confusion, which may lead to errors in results.

Additionally, current microfluidic systems have poor portability due to complicated external controls, making them somewhat impractical for clinical use. Clearly, a portable microfluidic system capable of rapid diagnosis which is able to analyze genetic, protein and cell composition of a sample in parallel for specific diseases from a relatively small sample is needed. Such a system or a method of using such a system, that is, using a single microfluidic chip integrated into a unique portable microfluidic platform, would provide improved diagnostic accuracy, allow for frequent monitoring and would be suitable for easy use in clinical settings.

SUMMARY OF THE INVENTION

According to a first aspect of the invention, there is provided a sample analysis system comprising:
a microfluidic chip comprising:
a sample input for applying a sample to the chip;
a separator connected to the sample input by a separation channel;
one or more reaction channels, each reaction channel being connected to the separator and being of varying length, each reaction channel,
each said reaction channel being further connected to a respective outlet.
a reagent input;
a thermoelectric semiconductor arranged to heat or cool one or more of said channels;
an LED array arranged to emit radiation over specific wavelengths to the microfluidic chip;
a detector arranged to detect fluorescence from said microfluidic chip; and
a control unit arranged to control the valves and analyze results from the detector.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is an integrated microfluidic platform that detects genetic, bacterial, viral, DNA, protein and/or cellular markers. The system comprises microfluidic chips for handling samples and the corresponding control and detection systems.

Current disease diagnosis methods commonly rely on detection of markers through separate specialized assays (e.g. PCR-based gene detection; DNA and protein microarrays; ELISA; cell assays). The use of different assays requires larger quantities of samples as well as multiple specialized facilities. Accordingly, methods such as this are ill-suited for point of care analysis, for example, at the location of patient clinical diagnosis and treatment.

This invention addresses this problem by providing a system and a method for performing bacterial, viral, genetic, DNA, protein and/or cell detection assays simultaneously on a single microfluidic chip from a relatively small amount of a single sample within a portable station that integrates all mechanical, thermal, optical and electronic control, detection and analysis modules, as discussed below.

Furthermore, as discussed herein, the sample size required for the device and method is significantly less than traditionally collected from patients for analysis. For example, the device and the method can carry out some analyses using only a drop of blood, for example, a sample of approximately 10 µl. As will be appreciated by one of skill in the art, in some embodiments, a sample can be eluted, for example, from a blood spot or blood stain and analyzed. In other embodiments, where relatively rare cells are to be detected, a larger volume sample may be needed.

Features of the Integrated PCR:
1. On-chip sample separation and preparation
2. PCR
3. Protein arrays
4. Cell capturing and staining Specifically, in preferred embodiments, the sample analysis system comprises a microfluidic chip, a thermoelectric semiconductor, an LED array, a detector and a control unit.

In some embodiments, the microfluidic chip comprises a sample input for applying a sample to the chip; a separator connected to the sample input by a separation channel; at least one reaction channel or one or more reaction channels or at least two reaction channels, or two or more reaction channels, each reaction channel being connected to the separator and being of varying length, wherein each said reaction channel is further connected to a respective outlet.

In some embodiments, as discussed below, some of the channels include at least one valve for controlling flow of the sample and reagents.

Figure 1:
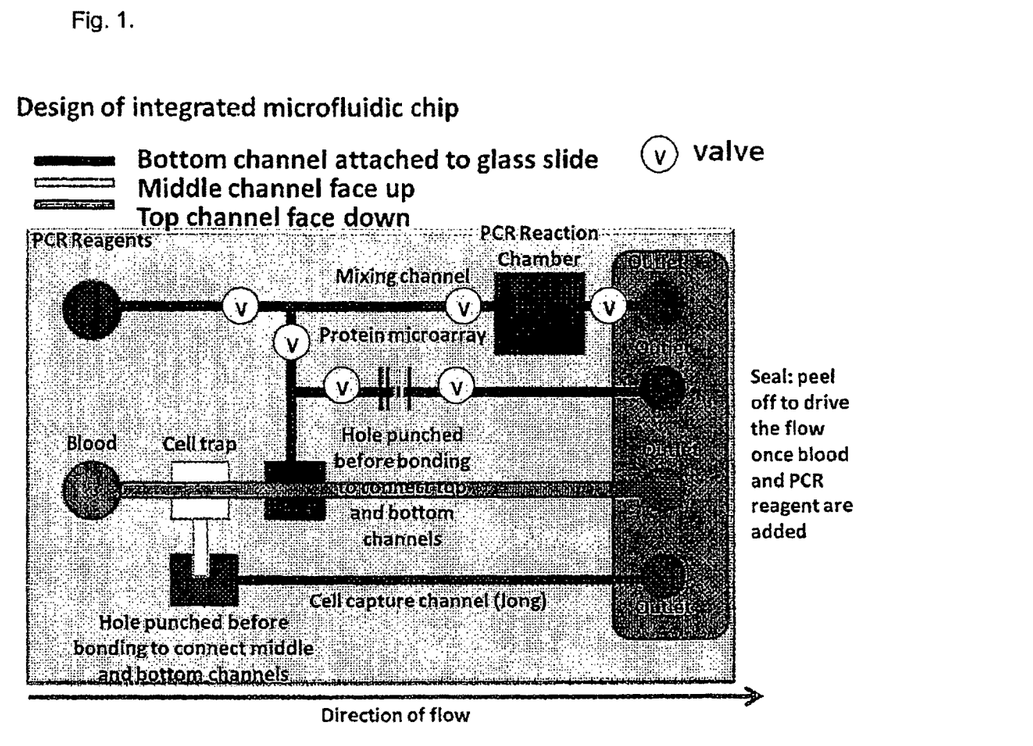
FIG. 1. Illustration of the integrated MFC for PCR, protein and cell assays.

In a preferred embodiment, the separator is a gravity trap, as shown in FIG. 1.

Specifically, as shown in FIG. 1, a sample such as blood is applied to the sample input 10 which is connected by separator channel 12 to separator 14.

In preferred embodiments, the sample input 10 and the separator channel 12 are at the "top" or highest layer of the microfluidic chip, as discussed herein.

As a result of this arrangement, as the sample, for example, the blood sample, encounters the separator 14 which is at a middle layer of the chip, it acts as a cell trap or gravity trap and causes the blood cells in the blood sample to "drop" from the middle layer down to the bottom layer within the microfluidic chip 1 via cell trap channel 16 to the cell reservoir 17. The blood cells are then passed from the cell trap channel to a cell detection channel 18 which is in the bottom channel of the microfluidic chip, as discussed herein.

In the embodiment shown in FIG. 1, the remaining sample that exits the separator, in this example, plasma, is passed to the fluid reservoir 19 and then is split among a plurality of channels, for example a mixing channel 20 which is connected to a PCR reaction chamber 22, as discussed herein; a protein detection channel 24, for example, an ELISA channel or antibody binding channel or other similar channel for analyzing proteins or peptides, as discussed below; and a RNA analysis channel 26.

As will be appreciated by one of skill in the art, in the example discussed above and shown in FIG. 1, channels are provided for PCR (DNA) analysis, protein analysis, cellular analysis and RNA analysis. As discussed herein, additional channels may be added for additional DNA, protein, cellular and/or mRNA analysis, or some channels may be substituted for a second or third channel of similar type, depending on what the sample is being analyzed for, as discussed below.

In some embodiments, as illustrated in FIG. 1, the cell detection channel 18 terminates in a cell outlet 36; the mixing channel 20 and the PCR chamber 22 terminates at a PCR outlet 30; RNA analysis channel 24 terminates at RNA outlet 34; and protein detection channel 24 terminates at protein detection outlet 32.

There is also provided at least reagent inlet 28 for applying reagents such as PCR reagents to the microfluidic chip, as shown in the accompanying figures.

Figure 2:
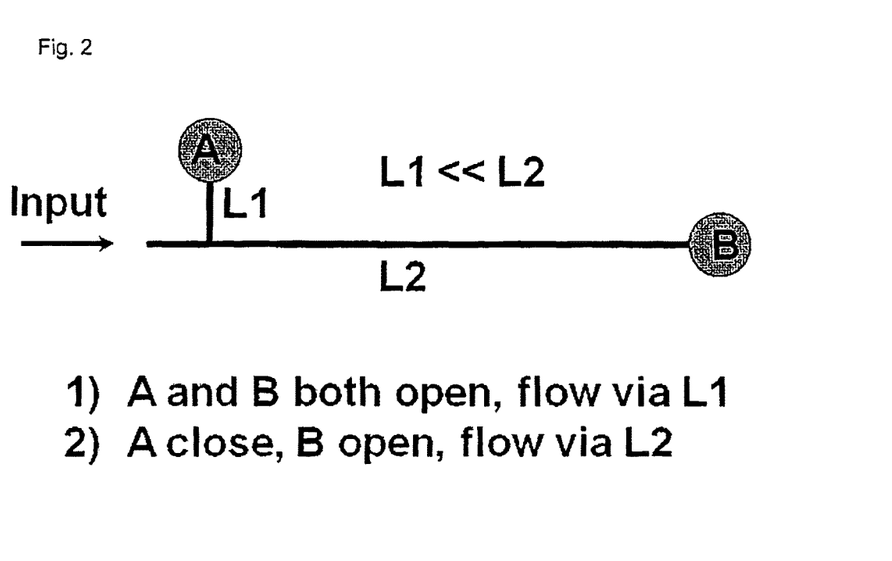
FIG. 2. Illustration of the fluidic resistance based on-chip valves
FIG. 3. Schematic diagram of microfluidic chip
FIG. 4. Schematic diagram of one embodiment of the detection system.

As shown in FIG. 1, the microfluidic chip includes a plurality of valves 38 for controlling flow along at least some of the reaction channels, as discussed herein. Specifically, as shown in FIGS. 1 and 2, the channels are preferably of different lengths so that opening of specific valves will allow control of the flow of sample along specific pathways. For example, as shown in FIG. 2, if both valves A and B are open, sample will preferentially flow along the shorter channel (L1). However, if valve A is open and valve B is closed, sample will flow along the longer channel (L2).

In preferred embodiments, the microfluidic chip is used for the analysis of a sample for the presence of biological markers of interest.

The thermoelectric semiconductor heats or cools or is arranged to heat or cool one or more of said channels. As will be appreciated by one of skill in the art, as a result of this arrangement, the temperature within the channels and reaction chambers can be modified so that ideal reaction conditions are maintained. For example, PCR reactions require thermal cycling whereas antibody binding is typically carried out at lower temperatures; however, as a result of the use of the thermoelectric semiconductor, these different reactions can be carried out simultaneously in the microfluidic chip by applying different temperature conditions to different regions of the microfluidic chip, as discussed herein.

The LED array emits or is arranged to emit radiation at a specific range a specific set of wavelength(s) of interest to the microfluidic chip. In preferred embodiments, the LED array subjects the microfluidic chip to a plurality of wavelengths in sequence, as discussed below.

The detector detects or is arranged to detect fluorescence emitted from the resulting reactions in the channels of the microfluidic chip and report the results to the control unit.

The control unit controls or is arranged to control the valves on the channels, thereby controlling the flow of sample and reagents throughout the chip. The control unit also analyzes results from the detector.

As discussed below, the flow of the sample through the microfluidic chip may be regulated by differential pressure. Preferably, the differential pressure is generated by having channels of different lengths, as discussed below.

As discussed herein, the separator separates blood into cells and plasma and may be any suitable separator known in the art, for example, a gravity trap.

The system may include a plurality of dedicated reaction channels, as discussed above, for example, one, two, three, four or more reaction channels. The reaction channels may be, for example, a PCR reaction chamber, a cell detection chamber and/or a protein detection chamber, as discussed below.

Accordingly, in some embodiments of the invention, there is provided a microfluidic chip comprising:
a sample input for applying a sample to the microfluidic chip;
a separator connected to the sample input by a separator channel, said separator separating a sample into cells and fluid;

a cell analysis channel receiving the cells from the separator; and at least one analysis channel receiving the fluid from the separator.

The analysis channel may be selected from the group consisting of a DNA analysis channel, an RNA analysis channel, an antibody detection channel, a protein analysis channel and combinations thereof.

Accordingly, in some embodiments of the invention, there is provided a microfluidic chip which comprising:

at least three layers: a top layer, a middle layer and a bottom layer;

a sample input for applying a sample to the microfluidic chip, said sample input being at the top layer of the microfluidic chip;

a separator connected to the sample input by a separator channel, said separator separating a sample into cells and fluid, said separator channel being at the top layer of the microfluidic chip and said separator being at the middle layer of the microfluidic chip;

a cell analysis channel being at the bottom layer of the microfluidic chip and receiving the cells from the separator; and at least one analysis channel receiving the fluid from the separator.

The analysis channel(s) may be selected from the group consisting of a DNA analysis channel, an RNA analysis channel, an antibody detection channel, a protein analysis channel and combinations thereof.

There may be at least one, one or more, at least two, two or more, at least three, three or more or at least four analysis channels.

In preferred embodiments, the microfluidic chip is a sealed chip and/or a chip that is prepared under vacuum prior to use within the system.

According to a further aspect of the invention, there is provided a method of analyzing a sample comprising:

providing a vacuum-sealed microfluidic chip which comprises:
  a sample input for applying a sample to the microfluidic chip;
  a separator connected to the sample input by a separator channel, said separator separating a sample into cells and fluid;
  a cell analysis channel receiving the cells from the separator; and
  at least one analysis channel receiving the fluid from the separator. and
  at least one reagent input;

applying a sample comprising cells and fluid to the sample input;

releasing the vacuum seal of the of the microfluidic chip such that the sample flows into the separator channel;

separating the sample via the separator into cells and fluid;

passing the cells to a cell analysis channel;

separating the fluid into one or more analysis channels, said analysis channel being selected from the group consisting of a DNA analysis channel, an RNA analysis channel, an antibody detection channel, a protein analysis channel and combinations thereof;

incubating the respective channels at suitable temperatures for a suitable period of time with a thermoelectric semiconductor to drive reactions to completion;

emitting radiation over at least one suitable wavelength to the microfluidic chip via an LED array;

detecting florescence from the microfluidic chip with a detector; and analyzing results from the detector.

According to a further aspect of the invention, there is provided a method of analyzing a sample comprising:

providing a vacuum-sealed microfluidic chip which comprises:
  at least three layers: a top layer, a middle layer and a bottom layer;
  a sample input for applying a sample to the microfluidic chip, said sample input being at the top layer of the microfluidic chip;
  a separator connected to the sample input by a separator channel, said separator separating a sample into cells and fluid, said separator channel being at the top layer of the microfluidic chip and said separator being at the middle layer of the microfluidic chip;
  a cell analysis channel being at the bottom layer of the microfluidic chip and receiving the cells from the separator;
  at least one analysis channel receiving the fluid from the separator; and
  at least one reagent input;

applying a sample comprising cells and fluid to the sample input;

releasing the vacuum seal of the of the microfluidic chip such that the sample flows into the separator channel;

separating the sample via the separator into cells and fluid;

passing the cells to a cell analysis channel;

separating the fluid into one or more analysis channels, said analysis channel being selected from the group consisting of a DNA analysis channel, an RNA analysis channel, an antibody detection channel, a protein analysis channel and combinations thereof;

incubating the respective channels at suitable temperatures for a suitable period of time with a thermoelectric semiconductor to drive reactions to completion;

emitting radiation over at least one suitable wavelength to the microfluidic chip via an LED array;

detecting florescence from the microfluidic chip with a detector; and analyzing results from the detector.

As will be appreciated by one of skill in the art and as discussed herein, the respective channels and chambers are preferably pre-loaded with suitable reagents.

For example, the PCR channel and the microRNA channel may comprise suitable primers for amplification of the target nucleic acid sequence or molecule, as well as the necessary reagents for amplification thereof, including enzymes, as discussed below.

Furthermore, the cell analysis channel may comprise antibodies for binding specific cell surface antigens or peptides or may comprise ligands specific for specific cell surface peptides or antigens or for specific types of cells.

The peptide analysis channel may comprise specific antibodies or ligands to bind specific peptides of interest.

Other suitable reagents and means for their detection using fluorescence will be readily apparent to one of skill in the art.

Furthermore, the temperatures, reaction times and conditions for these reactions are well known to one of skill in the art. For example, PCR amplification requires thermal cycling while peptide-peptide interactions such as peptides binding to ligands or antibodies requires lower temperatures.

Finally, as discussed below, it is important to note that the analysis carried out in each of the channels is related to diagnosing, detecting or monitoring a specific disease or disorder.

The system can be used in diagnostic applications for both human and animal diseases. The device can easily be located near the patient or animal undergoing diagnosis and treatment for a variety of disease states requiring either genetic, protein or cell analysis. As will be appreciated by one of skill in the art, in some cases, the system can be used on an on-going basis to determine how treatment is progressing or what impact certain therapeutic steps are having.

Figure 3:
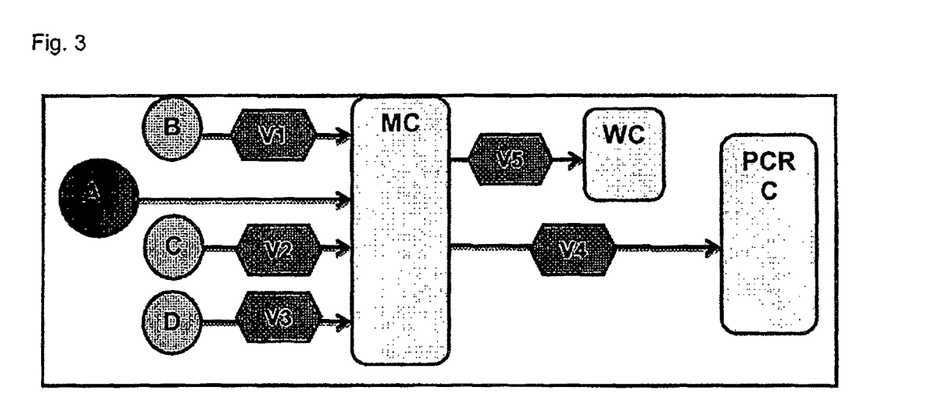

The microfluidic chip is arranged to separate samples into the required formats suitable for simultaneous genetic, protein and cell detection. That is, the chip is capable of on-chip blood sample separation into cells and plasma and directs each sample to specific detection chambers on the chip via parallel channels. The chip comprises multiple modules based on specific physical and chemical principles for sample separation, PCR reaction, protein microarray detection and antibody-based cell detection, and has specially designed inlets and outlets for sample loading and fluidic controls (FIG. 3).

The control and detection system is specifically designed to work with the microfluidic chip described above. The system comprises mechanical features for fitting the microfluidic chip, as discussed herein. The device consists of multiple layers of interconnected channels that would allow separation of different components of the samples (e.g. plasma and cells), which are directed to separate chambers for assays (PCR, protein and cell). This allows for separate reaction control of different assays at different regions of the device as discussed herein. In addition, on-chip valves are incorporated for flow and reaction controls and thermal control modules for PCR reactions and protein/cell staining.

As discussed above, the system allows for different temperatures to be applied to different regions of the chip. In a preferred embodiment, a copper thermo-electric semiconductor is used to heat or cool the desired area. In some embodiments, the sample is housed in glass and the semiconductors sit under the glass housing As discussed above, there are also provided optical modules for detecting signals from samples (e.g. fluorescent signals from PCR analysis, protein microarray and cell staining, etc.).

Figure 4:
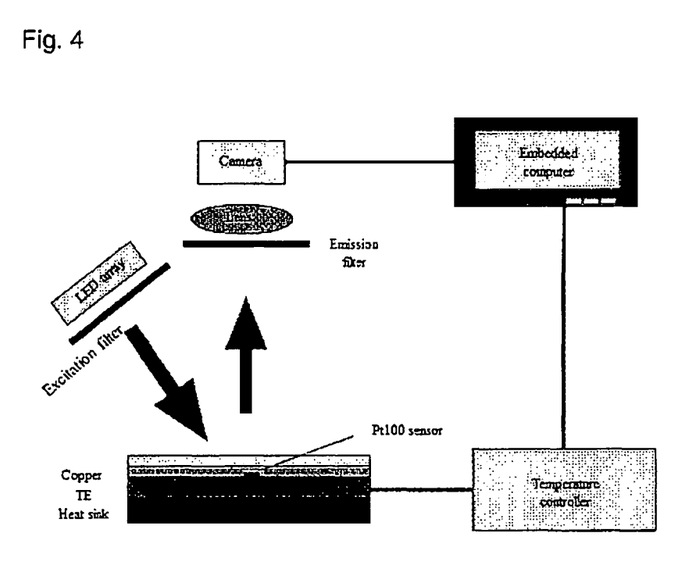

Typically, fluorescence is between 380 and 520 nanometers. In some embodiments, an LED array is used with the microfluidic chip as shown in FIG. 4. In one embodiment, each LED in the array emits energy at a specific wavelength and is activated in sequence. Alternatively, in other embodiments, each representative LED in the array may be arranged to emit at at one of a plurality of desirable wavelengths.

It is of note that suitable wavelengths for use in detection are very well known in the art and will be readily apparent to one of skill in the art.

As discussed above, the system also includes a detector which measures the fluorescence and reports this information to the control unit for data processing for rapid analysis.

The system is designed for high-throughput testing to achieve statistical accuracy and to allow parallel control testing.

Most microfluidic chips currently on the market use pumps and are expensive. However, in this invention, fluids are moved around the chip based on pressure differences. Specifically, a low pressure microfluidic chip (MFC) is manufactured and then sealed (e.g. using an adhesive sheet). Subsequently the sample, for example DNA, cells or a virus will be guided into the device by controlled pressure difference between the inlet and the outlet of the device. The channels in the MFC are then opened. In some embodiments, a tab or seal is used. In other embodiments, tubing and/or an electronic switching wall is used. In other embodiments, agarose gel is used to close the channel once the sample is loaded to the reaction chamber. Within the MFC, the principles of microfluidics are used to design the channels to ensure the mixing of fluids as desired, as discussed herein.

The microfluidic device is capable of on-chip blood sample separation, specifically, separating the components of the blood into multiple channels. One channel comprises cells for the detection of antibodies. Specific cell types are first captured based on specific cell adhesion molecules and the use of the corresponding capturing antibodies coated in the channel. The identity of the captured cells is verified by immunostaining. In some embodiments, if necessary, it is possible to use the captured cells for downstream protein and PCR analysis to further verify their identity.

In some embodiments, other channel(s) comprises plasma. The plasma channel from the separator may be further divided into a DNA channel and a microRNA channel for analysis of the plasma.

Current methods of microfluid management use either air pressure or temperature differences to control the flow of fluids. However, with a multi-channel system, neither of these options would be suitable as these would require another layer to be added to the MFC making the chip large, complex, and likely unreliable.

In the method described herein, as discussed above, "differential pressure" is used to separate the blood into the appropriate channels and manage the time required for analysis (e.g. the plasma needs to stay in one part or region of the chip for a set amount of time for the reactions to go towards completion).

Prior to use, the microfluidic chip (MFC) is placed in a vacuum chamber and subsequently sealed to maintain low pressure in the channels. When used, the seal is released to draw the sample from the inlet into the device. The on-chip mixing and reaction control are achieved using on-chip valves. The fluidic resistance based on-chip valves are used to control the flow and reaction. More specifically, each valve consists of bifurcated output channels with significantly different channel length (FIG. 2) and thus creates differential pressure between the two flow paths. Depending on if the short channel is open, the sample can be controlled to either flow into the reaction chamber via the long channel (when the short channel is closed) or flow out from the short channel (when the short channel is open) and thus prevent further flow into the reaction chamber.

Thus, in this manner, the differential pressure is accomplished by a stable mechanical method by managing the length of the channels. With a longer and shorter channel, differential pressures will result which will be stable and predictable. An alternative approach to achieve and control the differential pressure is to insert tubing through the channel and mechanically open and close channels.

In this manner, a microfluidic device that is capable of on-chip blood sample separation and compartmentalization with passive flow control, and high-throughput mechanical on-chip valves is developed.

Most current on-chip valves are based on air or thermal actuation and in many cases require multiple aligned layers of channels so the control channel can open or close the corresponding fluid channel.

The control and detection system is arranged to control the on-chip valves for example by applying programmable mechanical pressure to actuate the on-chip valves and/or pumps.

In some embodiments, the device has separate temperature controls for different channels on the chip.

If fluorescent optical detection is to be used for different assays, it is necessary to make sure there is no cross-interference from the wavelengths used for excitation and reporting. However, it is noted that this can easily be done by careful selection of reagents. In some specific embodiments in which more complex analysis is carried out, multiple cameras and/or detection fibers may be used for different channels; a rotating stage may be used to present different channel(s) to the detection area(s); or different fluorescent molecules/colors may be used for different assays As described above, this invention provides users with the ability to perform rapid parallel genetic, protein and cell detection for diagnosing specific disease from a relatively small amount of sample on an integrated and portable microfluidic platform and thus allows for improved diagnosis accuracy, frequent monitoring and is well suitable for ease use in clinical settings. Integrating genetic, protein and cell detection on a single microfluidic chip will significantly improve disease detection accuracy and efficiency. This is impractical with current methods that detect single markers separately.

In some embodiments, a sample, for example a blood sample, is passively driven into the device by a controlled pressure difference between the inlet and the outlet. Blood cells and plasma are separated into different channels using the multi-layer structure design and the separator. As discussed above, plasma is separated into different channels for protein assays and PCR reaction.

Other reagents (e.g. PCR reagents, washing buffer, antibodies, etc.) are manipulated by on-chip valves and/or pumps (e.g. air pressure actuated valves and pumps based on multi-layer PDMS devices, etc.), as discussed above.

As discussed above and as will be readily apparent to one of skill in the art, the design and fabrication of microfluidic chips, the operation processes and the associated control/detection systems can be specifically developed for specific diseases and sample types, but all under the concept of this invention. For example, systems specific for breast cancer, liver cancer, or prostate cancer can be designed, each with its own markers. Similarly, systems can be arranged for detection of chronic disease indicators, for example heart and kidney disease. Similarly, systems can be arranged for the detection of bacteria such as MRSA.

For use, the chip is inserted into the machine. The control ports are fitted to the corresponding adaptors in the machine that can apply controlled mechanical operations. Specific channels of the device are aligned with the corresponding reaction control (temperature) and detection (optical) components of the machine.

To operate the system, the blood sample is added to the inlet port of the device. All control lines are connected to the device and reagents are loaded to the storage wells in the device (e.g. PCR reagents, washing buffer, etc.) or pre-coated in the device (e.g. antibodies for protein assays or cell capturing assays, etc.). The outlet cover of the device is removed to initiate passive flow of the blood sample into the device. If needed (e.g. CTC detection), off-chip pumps will be used to process large amounts of blood samples. On-chip valves and pumps are operated subsequently to manipulate other reagents for different assays. Temperature control and data acquisition/analysis are controlled by the Super PCR system.

EXAMPLE

1. A whole blood sample is taken from the patient and mixed with regents to prevent clogging or coagulation.
2. The blood is added to the device from the inlet well.
3. A seal is removed from the outlet of the device to draw the blood sample into the channel. The device is inserted into the machine.
4. At this point, fluidic valves, thermal and optical controls systems start operation.
5. Cells and plasma are separated by the gravity trap and flow into different channels.
6. Cells are directed to the capture channel coated with capturing antibody.
7. Once captured, cells are stained with detection antibody and the fluorescently-tagged antibody is detected by the system.
8. Plasma is separated to the protein chamber and PCR chamber.
9. Protein markers are captured in the capturing antibody coated channel and optically detected.
10. miRNA is detected by on-chip PCR in the PCR reaction chamber. For this, on-chip miRNA isolation and enrichment, and mixing with PCR reagents steps may be needed. Thermal control is critical. The PCR signal is detected optically.
11. The data from the control unit is then analyzed.

Such integrated applications require accurate control of complex fluidic samples. In addition, each assay (PCR, protein and cell assay) requires different reaction controls (e.g. temperature, chemical mixing, staining and washing steps, etc.) and follows different timelines, leading to high design requirement for the system. Finally, detection accuracy requires multiple repeats of the assays as well as appropriate positive and negative controls on a single chip and thus demands that the system have high-throughput capabilities Below is a further example of how the system can be used for a 3-in-1 test that includes genetic, protein and cell based tests from a single initial blood sample on a single chip.

The system consists of:

The device/machine

The test kit including the microfluidic chip.

The device is plugged into an electrical source in a standard clinical lab but does not require a clean room.

The test kit is the microfluidic chip. The chip comprises:
1. Physical channels to manage the flow of fluids (including buffers and blood sample)
2. Solid phase reagents
3. Buffers
4. At least three reaction chamber channels, for example, one for DNA, one for protein and one for cells.

The chip is sealed. The reagents and the buffers are situated in specified locations inside the chip.

PCR Testing for DNA

To identify multiple DNA examples using PCR, the reagents in the chip can be configured in at least two ways.
Option 1.

All of the PCR-related reagents are placed in one storage well within the chip. In this case, the specific reagents for specific genes would fluoresce in different colours. For example, gene A would fluoresce pink, while gene B would fluoresce blue and the control system would identify which gene is present based on the colour detected.

Option 2

Each PCR reagent is placed in a specific and discrete storage well inside the chip. All reagents could therefore fluoresce the same colour in PCR. Using the same example above, gene A and B could each fluoresce at yellow, but if the gene A reagent is in Channel A and gene B reagent in Channel B, then it is the location of the fluorescence that identifies the presence or absence of the gene in the sample.

Selection of the Reagents.

To enable the system to detect multiple biomarkers, the user must be able to select the reagents to be used in the test kit. One approach would be to enable each user to customize their specific order. For example, a user could select from a number of reagents, for example, 50 reagents. The customer could select which reagents are placed inside their test kit, for example, up to five reagents. The chips would then be manufactured with those specific reagents placed inside the chip. The chip would then be sealed, and transported to the customer.

Before the blood sample is added to the chip, the user must "activate" the chip. Reagents are held in a dedicated compartment on the chip. Reagents are stored in a solid form. To interact with the blood sample, the reagents must liquefy. The buffers are used to liquefy the reagents. As will be appreciated by one of skill in the art, there are many possible methods to manage the flow of the buffer and direct the buffer(s) to the reagent(s). These include but are by no means limited to pressure-based methods, vacuum-based methods or mechanical-based methods. In one embodiment, the user pulls tubing out of the chip which removes a physical barrier in the chip that separates compartments of the chip (open the valve). Once the wall is removed, the buffers mix with the reagents. The user will need to wait for the reagents to become liquid before placing the blood sample into the chip.

Blood is drawn using a standard technique such as a finger prick. A pipette may be used to draw the blood and place the blood into the inlet valve on the chip. Once the blood is in the inlet valve, a second tubing may be removed. This removes the barrier that separates the blood sample from the reagent and buffer solution. In addition, another tab is removed from the outlet to allow flowing of the samples and reagents. Once the pressure seal is torn off, the blood sample is drawn into the chip. Discussed below are two possible design embodiments, based on the desired analysis.

Option 1:

This embodiment is utilized if a user is looking for samples that are not resident inside the cell membrane, but rather are found in the plasma. For example, circulating microRNA is in the plasma. In this embodiment, once the seal tab is peeled to draw the blood into the chip, the plasma is separated from the cells, for example, using a gravity cell trap as cells are heavier than plasma and the cells would fall into a gravity trap. The plasma would not fall into the gravity trap and would continue to flow down the channel and reach a solution comprised of the buffer(s) and reagent(s). The channel continues to the reaction chamber.

Option 2:

In an embodiment in which a user is looking for targets that are resident inside the cell membrane, the chip would not have a cell trap. Instead, the chip would use a lysis process to break down the cell membrane and the material inside the cell walls would continue along the channel to the solution of buffers and reagents. The lysis process employs a buffer which sits in a compartment near the intake valve for the sample (blood). As discussed above, pull tubing will be used at the intake valve and only pulled once the blood sample is in the chip. Washing steps and RNA/miRNA enrichment/separation steps will then be performed on the chip. These steps will be operated using similar on-chip valves and flow driving method together with required reagents/buffers and membranes. The final sample will encounter the PCR reagent and buffer solution as the channel continues to the reaction chamber.

Once the desired elements of the blood sample and the solution reach the desired reaction chamber, four events will be triggered.

1. The thermo cycler will engage and apply variable heat to amplify the PCR sample according to the reagents used (e.g. reagent A will amplify sample A if it is present).
2. The LED sequence begins providing different wavelengths of illumination such that the desired wavelength spectrum is applied to the sample.
3. Optical sensors detect the presence or absence of fluorescence (colour and/or location as discussed above).
4. The control unit processes the outputs of the optical sensors and generates a report.

Protein Test Data

From the same blood sample as in the PCR test example, after separation of plasma and cells, the plasma sample flows through two distinct paths. One path is for PCR as before, the other is for a protein assay. The protein reaction chamber is coated with one or more protein-capturing antibody(s) to capture specific proteins. Once the protein is captured, fluorescently labeled detection reagents are released to flow through the reaction protein chamber Then, three events are triggered.

1. The LED sequence provides different wavelengths of illumination such that the desired wavelength spectrum is applied to the sample.
2. Optical sensors detect the presence or absence of fluorescence (colour and/or location).
3. The control unit processes the outputs of the optical sensors and generates a report.

Note that if protein is from cells, then after cells are lysed, the lysate will be used for protein assay.

Cell Test

The cells separated from the blood sample flow to another reaction chamber for cell assay. The cell reaction chamber is coated with cell capture molecules to capture cells. If needed, once the cell is captured, detection reagents (fluorescently labeled) will be released to flow through the reaction cell chamber Option 1:

If only detecting the captured cells without fluorescent labeling, then the reaction cell chamber will be directly imaged to count cells, and the control unit generates a report.

Option 2:

If the captured cells are fluorescently labeled to further detect cell specificity, then three events will be triggered.

1. The LED sequence provides different wavelengths of illumination such that the discussed wavelength spectrum is applied to the sample.
2. Optical sensors detect the presence or absence of fluorescence (colour and or location).
3. The control unit processes the outputs of the optical sensors and generates a report.

The scope of the claims should not be limited by the preferred embodiments set forth in the examples, but should be given the broadest interpretation consistent with the description as a whole.

The invention claimed is:

1. A method of analyzing a sample comprising:
providing a vacuum-sealed microfluidic chip comprising:
at least three layers: a top layer, a middle layer and a bottom layer;
a sample input for applying a sample to the microfluidic chip, said sample input at the top layer of the microfluidic chip;
a gravity trap separator connected to the sample input by a separation channel, said gravity trap separator separating a sample into cells and fluid, said separation channel at the top layer of the microfluidic chip and said gravity trap separator at the middle layer of the microfluidic chip;
a cell detection channel at the bottom layer of the microfluidic chip and receiving the cells from the gravity trap separator;
at least one analysis channel, each at least one analysis channel connected to the separation channel to receive the fluid therefrom, each said at least one analysis channel being selected from the group consisting of a DNA analysis channel, an RNA analysis channel and a protein analysis channel;
each said at least one analysis channel and said cell detection channel being further connected to a respective outlet; and
reagent inlets, each said inlet being connected to one respective analysis channel or the cell detection channel and being pre-loaded with reagents for the respective channel, wherein reagents for the DNA analysis channel and the RNA analysis channel comprise primers for amplification of a target nucleic acid sequence and reagents for the cell detection channel comprise antibodies or ligands for binding cell surface antigens or cell surface peptides or specific types of cells; and reagents for the protein analysis channel comprise antibodies or ligands for binding to peptides of interest;
applying a sample comprising cells and fluid to the sample input;
releasing the vacuum seal of the microfluidic chip so that the sample flows into the separation channel;
the gravity trap separator interacting with the sample from the separator channel and separating the sample into cells and fluid, the gravity trap dropping the cells down to the bottom level of the microfluidic chip and into the cell detection channel and the fluid passing from the separation channel into the at least one analysis channel;
the cells binding to antibodies or cell adhesion molecules in the cell detection channel while incubating the cell analysis channel at a temperature suitable for antibody binding via a thermoelectric semiconductor;
staining the bound cells with fluorescently-tagged detection antibodies;
if the at least one analysis channel is a DNA analysis channel or an RNA analysis channel, mixing the fluid with primers and reagents for amplification of the target nucleic acid sequence and subjecting the mixture to thermal cycling via the thermoelectric semiconductor;
if the at least one analysis channel is a protein analysis channel, capturing the proteins of interest with antibodies and then binding with fluorescently labeled detection reagents;
emitting radiation over at least one wavelength to emit fluorescent signals to the microfluidic chip with an LED array;
measuring fluorescence from the cell detection channel and the at least one analysis channel with a detector, said detector reporting fluorescence results to a control unit; and
the control unit analyzing the fluorescence results from the sample.

2. The method according to claim 1 wherein flow of the sample through the microfluidic chip is regulated by differential pressure.

3. The method according to claim 2 wherein the differential pressure is generated by the respective channels being of different lengths, at least one of the channels including a valve for regulating flow along said one of the channels.

* * * * *